Oct. 8, 1946. H. C. SWIM Plant Pat. 712
ROSE PLANT
Filed Dec. 18, 1945
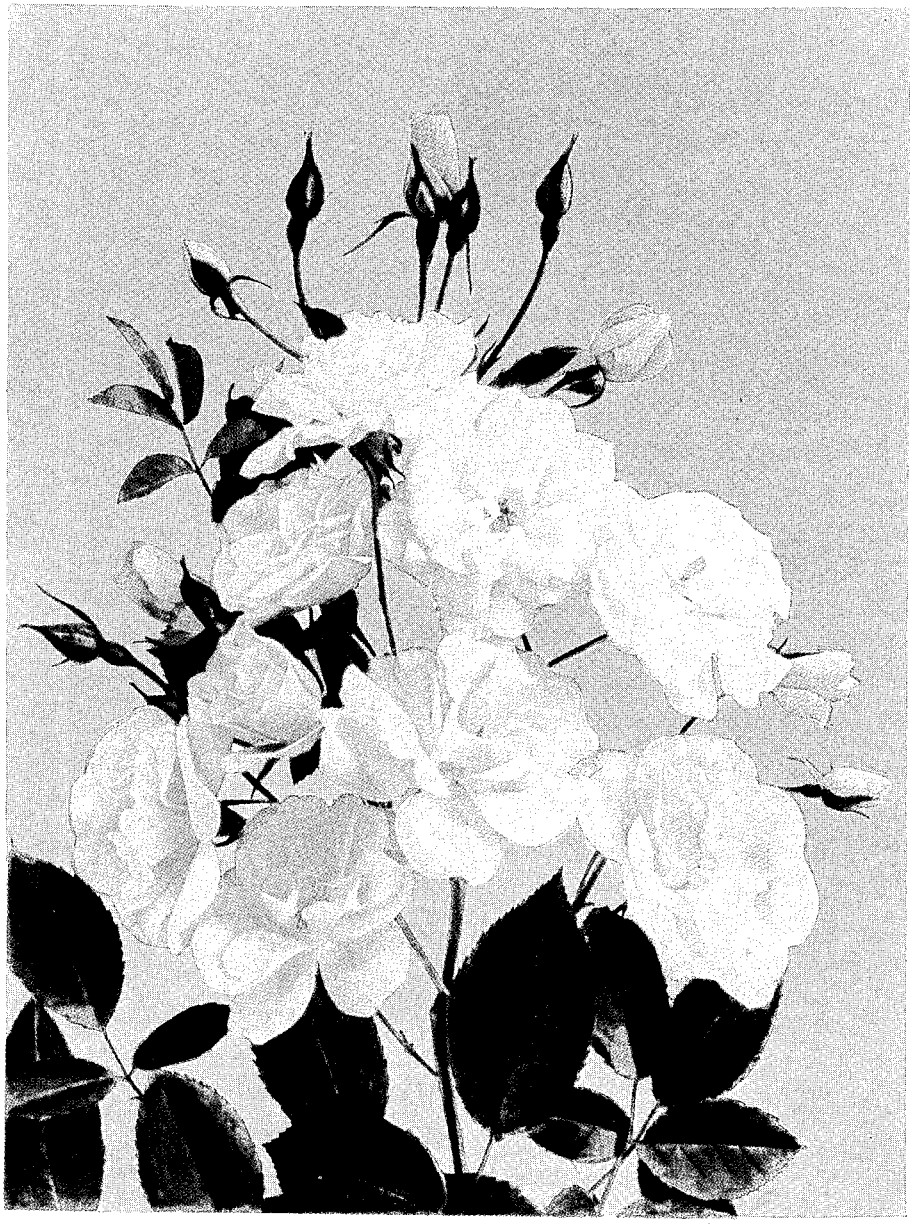
Inventor
H. C. Swim
By Robb & Robb
attorneys Patented Oct. 8, 1946

Plant Pat. 712

UNITED STATES PATENT OFFICE

712

ROSE PLANT

Herbert C. Swim, Ontario, Calif., assignor to Armstrong Nurseries, Inc., Ontario, Calif., a corporation of California Application December 18, 1945, Serial No. 635,663

1 Claim. (Cl. 47—61)

The present invention relates to a new and distinct variety of polyantha rose plant, a seedling originated by open pollination of the variety "China Doll," Plant Patent No. 678.

This new rose most nearly resembles its parent in general appearance of the plant, but differs from it and from any known rose of its type in respect to a number of its characteristics. The important points of difference may well be summarized as follows:

(*a*) In habit of growth, it is much more loose and graceful; almost twice as tall and twice as broad;

(*b*) The trusses of bloom are broader, though not as compact, than those of "China Doll," and the individual flowers are slightly larger with fewer, but broader petals;

(*c*) The color of the flower is much lighter in hue than that of its parent and both bud and open flower have a distinctly different shape;

(*d*) The bud and half-open flower have a perfection of form not heretofore found in polyantha varieties. This form is similar to that of the well-known rose, "Cecile Brunner," but this new variety is generally considered to be an improvement on "Cecile Brunner" because of the much longer, more graceful buds, the deeper, more pronounced color, the greater number of bloom per cluster, the more compact, better foliaged plant and the fragrance found in the flowers of this new variety;

(*e*) The color of the flower is of a shade of pink which makes it particularly suitable for use as an outdoor rose to supply flowers for corsage work, to which work the form of the flower above referred to particularly lends itself;

(*f*) The new rose is further characterized as to novelty by the very large size of the trusses in which the flowers are borne, the handsome, light-green, glossy foliage, highly resistant to mildew and sufficiently abundant to form an excellent and attractive background for the flower trusses which protrude through the foilage mass;

(*g*) Owing to the free-blooming trait of the new rose, its freedom from unsightly fading, and the tendency for the petals to drop off cleanly, it is especially adapted for use as a dwarf hedge, particularly in mild climates, and the adaptability for such decorative use and for cut flowers is enhanced by the mild but pleasing fragrance which is found but rarely in polyantha varieties.

Asexual reproduction shows that these characteristics hold true through succeeding propagations.

In the drawing:

The illustration shows a fragmentary portion of a plant of this new variety with one cluster or truss of the flowers in open condition, depicting the rounding characteristic of the cluster as a whole and the large number of flowers thereof, and a further cluster in the bud stage of development.

The following is a detailed description of the new variety, all references to color being in accordance with the R. F. Wilson's Horticultural Colour Chart, except where indicated to be in accordance with Ridgway's Color Standard and Nomenclature:

Type: Hardiness untested; dwarf; bush; seedling; for cut flowers and garden decoration.
Class: Hybrid; polyantha.
Breeding: Seedling.
*Seed parent.*—"China Doll."
*Pollen parent.*—Open pollinated.
Propagation: By budding, the only method tried so far.

*Flower*

Locality where grown: Ontario, California.
Flowers borne: Several to stem; in rounded cluster; on normal strength, medium length stems for polyantha plants.
Quantity of bloom: Abundant; outdoors.
Continuity: Nearly continuous during growing season.
Fragrance: Slight; musk to spicy.
Bud:
*Peduncle.*—Short; slender; erect; medium rough; numerous gland-tipped cilia and hairs. *Color*—Biscay Green, Plate XVII (Ridgway), to near Sulphine Yellow, Plate IV (Ridgway), on side exposed to sun.
*Before calyx breaks.*—*Size*—medium for polyantha. *Form*—short; ovoid; with foliaceous appendages; thin pubescence; gland-tipped cilia and glandular bloom on the surface of the bud; with slender foliaceous parts extending beyond the tip of the bud equal to ¼ or more of its length.
*As calyx breaks.*—*Color*—Camellia Rose, Plate 622, page 148. *Inner surface*—with fine, woolly tomentum. All margins of sepals have woolly tomentum and stipitate glands unless adjacent sepals cover margin. Otherwise, they have only woolly tomentum.

3

*As first petal opens.*—*Size*—medium for polyantha. *Form*—long; pointed to urn-shaped. *Color*—Outside: Camellia Rose, Plate 622/1, page 148. Inside: near Spinel Pink, Plate 0625/2, page 184.

*Opening.*—Opens up well. It is not prevented from opening by cold, wet or dry weather.

Bloom:

*Size.*—When fully open—large for polyantha; 1¾ inches to 2½ inches.

*Petalage.*—Double but the stamens not hidden; from 14 to 16 petals, plus 1 to 3 petaloids arranged regularly.

*Form.*—High centered at first; becoming open to cupped; petals remaining at first cupped with tips rolled outward; becoming later, at maturity, flat-cupped with tips rolled outward.

Petals: Medium thick; with inside satiny and outside slightly shiny.

*Shape.*—Outside—cuneate with apex flat. Intermediate—cuneate with apex flat. Inside—narrowly cuneate with apex flat.

*Color.*—Colors may be modified by being dotted or blotched with other colors in foggy weather.

This description of a newly opened flower was made from a rose grown outdoors in the month of October, 1945, at Ontario, California, in cool weather:

*Color.*—*Outside petal*—outside surface: near Phlox Pink, Plate 625/1, page 77; inside surface: near Neyron Rose, Plate 623/2, page 76. *Intermediate petal*—outside surface: near Phlox Pink, Plate 625/1, page 77; inside surface: near Neyron Rose, Plate 623/1, page 76. *Inner petal*—outside surface: near Phlox Pink, Plate 625/1, page 77; inside surface: near Neyron Rose, Plate 623/1, page 76.

This description was made from a rose that was open for three days outdoors in the month of October, 1945, at Ontario, California:

*Color.*—*Outside petal*—outside surface: near Phlox Pink, Plate 625/3, page 77; inside surface: near Rose Pink, Plate 427/1, page 126, dotted with Rose Opal, Plate 022/1, page 110, when affected by fog or dew. *Inside petal*—outside surface: near Phlox Pink, Plate 625/2, page 77; inside surface: near Neyron Rose, Plate 623/2, page 76.

*General color effect.*—Newly opened flower—near Neyron Rose, Plate 623/1, page 76. Three days open—near Neyron Rose, Plate 623/3, page 76, dotted with Rose Opal, Plate 022/1, page 110, on outside petals, as a result of fog.

*Behavior.*—Drop off cleanly; fading lighter; affected by hot weather by fading to lighter color.

*Flower longevity.*—On bush in garden three to four days in October. Cut roses grown outdoors, kept at living-room temperatures, two to three days in October.

*Reproductive organs*

Stamens: Medium number; arranged regularly about pistils, mixed with petaloids.

Filaments: Medium to long; from 1½ to 6 mm. long. *Color*—near Canary Yellow, Plate 2/2, page 2. Most with anthers.

4

Anthers: Medium large for polyantha; all open at once approximately. *Color*—(in newly open flower), near Lemon Yellow, Plate 4/2, page 4, to Buttercup Yellow, Plate 5/2, page 5, at margin.

Pollen: Moderately abundant; near Buttercup Yellow, Plate 5/2, page 5.

Pistils: Many for polyantha; 20 to 22 in number.

Styles: Even; medium length; 2 to 3 mm.; medium heavy; bunched; near Crimson, plate 22/2, page 22, to near Chartreuse Green, Plate 663/3, page 90.

Stigma: Clear, grayish white, more or less translucent.

Ovaries: All enclosed in calyx.

Hips: Ovoid; near Yellow Ocher, Plate XV (Ridgway), on side exposed to sun, to near Courge Green, Plate XVII (Ridgway), on side not exposed to sun; moderately smooth; walls thick, fleshy.

Sepals: Falling soon; moderately long; recurved. *Color*—inside: (sepals from newly-open flower)—near Deep Chrysolite Green, Plate XXXI (Ridgway), blushed with Cacao Brown, Plate XXVIII (Ridgway); outside: near Asphodel Green, Plate XLI (Ridgway), blotched with Cacao Brown, Plate XXVIII (Ridgway), particularly at margin.

Seeds: Few; large for polyantha; 2 to 3 seeds to the hip.

*Plant*

Foliage:

*Leaves.*—Compound of three to seven leaflets; normal to abundant; medium size; moderately thin, soft, glossy.

*Leaflets.*—Shape—ovate lanceolate, with apex acute; base obtuse; margin simply serrate.

*Color.*—*Mature*—upper surface: near Bice Green, Plate XVII (Ridgway); under surface: near Light Cress Green, Plate XXXI (Ridgway). *Young*—Upper surface: near Cress Green, Plate XXXI (Ridgway), with Brick Red, Plate XIII (Ridgway), shading, particularly at border; under surface: near Mignonette Green, Plate XXXI (Ridgway), with Brick Red, Plate XIII (Ridgway), shading, particularly at border of leaflet.

*Rachis.*—Heavy; upper side, grooved with few stipitate glands on edges; upper side, moderately prickly.

*Stipules.*—Medium long; medium wide; with medium long points, turning out at an angle of more than 45°.

*Disease.*—Resistant to mildew.

Growth:

*Habit.*—Dwarf; bushy; much branched.

*Growth.*—Free for polyantha.

*Canes.*—Medium weight.

*Main stems.*—Near Calla Green, Plate V (Ridgway). *Large prickles*—few; long; slightly hooked downward; with long, narrow base; near Hazel, Plate XIV (Ridgway). *Small prickles*—none. *Hairs*—none.

*Branches.*—Near Courge Green, Plate XVII (Ridgway). *Large prickles*—none. *Small prickles*—none. *Hairs*—none.

*New shoots.*—On weaker new shoots, near Parrot Green, Plate VI (Ridgway), with Pompeian Red, Plate XIII (Ridgway), shadings, on side exposed to sun. On strong new shoots, near Morocco Red, Plate I (Ridgway). *Large prickles*—none. *Small prickles*—none. *Hairs*—none.

I claim:

A new and distinct variety of rose plant of the polyantha class, characterized as to novelty by its loose and graceful habit of growth and development of large trusses of blooms, glossy foliage through which the bloom protrudes and thereby forms an attractive background for the flowers, the resistance to mildew of such foliage, the form, size, fragrance and color of the blooms, the large number of flowers per cluster and freedom of blooming, their freedom of the blooms from unsightly fading and their habit of dropping off cleanly, and the suitability of the plant generally for cut flowers and hedge purposes, substantially as shown and described.

HERBERT C. SWIM.